United States Patent

Timoteo

[11] Patent Number: 6,162,254
[45] Date of Patent: Dec. 19, 2000

[54] KNEE PROSTHESIS

[75] Inventor: Michel Timoteo, St Martin d'Uriage, France

[73] Assignee: Tornier S.A., Saint Ismier, France

[21] Appl. No.: 09/172,008

[22] Filed: Oct. 14, 1998

[30] Foreign Application Priority Data

Oct. 14, 1997 [FR] France ................................. 97 13073

[51] Int. Cl.$^7$ ................................................. A61F 2/38
[52] U.S. Cl. .................................... 623/20.33; 623/20.27
[58] Field of Search .................................. 623/20, 20.14, 623/20.15, 20.27, 20.28, 20.29, 20.3, 20.31, 20.32, 20.33, 20.34, 20.35

[56] References Cited

U.S. PATENT DOCUMENTS

| 5,271,747 | 12/1993 | Wagner et al. | 623/20 |
| 5,609,639 | 3/1997 | Walker | 623/20 |
| 5,658,342 | 8/1997 | Draganich et al. | 623/20 |
| 5,879,394 | 3/1999 | Ashby et al. | 623/20 |

FOREIGN PATENT DOCUMENTS

| 2663536 | 12/1991 | France . |
| 2719466 | 11/1995 | France . |
| 2735017 | 12/1996 | France . |
| WO 95/25484 | 9/1995 | WIPO . |
| WO 96/38103 | 12/1996 | WIPO . |

Primary Examiner—V. Miller
Assistant Examiner—Alvin Stewart
Attorney, Agent, or Firm—Greenblum & Bernstein, P.L.C.

[57] ABSTRACT

A knee prosthesis including a tibial plateau for anchoring to an upper end of a tibia. The tibial plateau includes an orifice and a projection. An insert is moveably disposed on the tibial plateau and is adapted to cooperate with a femoral component anchored to a lower end of a femur. The insert includes a boss and an indentation and moveably engages the tibial plateau such that the boss extends at least partially into the orifice and the projection shoulder extends at least partially into the indentation.

28 Claims, 5 Drawing Sheets

KNEE PROSTHESIS

BACKGROUND OF THE INVENTION

1. Field of the Invention

The invention relates to a knee prosthesis. More precisely, it relates to a knee prosthesis of the type comprising a tibial plateau anchored at the upper end of the tibia, the tibial plateau having an attached insert which is intended to cooperate with a femoral component anchored in the lower end of the femur.

2. Description of Background and Relevant Information

It is known that the insert, in most cases made of polyethylene, is subjected to repeated stresses exerted simultaneously by the tibial plateau and the femoral component during the movement of extension or flexion of the femur on the tibia, or vice versa, the permanent stresses leading to progressive wear and tear of the polyethylene.

To solve this problem, the document FR-A-2 735 017 has proposed a prosthesis, of the type in the present invention, comprising a median pin projecting from the upper face of the tibial element, the pin being engaged in a corresponding cavity formed on the lower face of the insert, and this in combination with arrangements in the form of lateral studs formed on the upper part of the tibial plateau and able to slide along two corresponding lateral cuttings provided on the lower face of the insert.

Although this configuration permits rotation of the femoral component on the tibial plateau during flexion of the knee, the insert nevertheless does not reproduce simultaneously the natural movement of the meniscus in the posteroanterior sense.

Likewise, the insert does not reproduce the movement of the meniscus on the tibial plateau during extension of the knee, namely a translation of the meniscus in the anteroposterior sense, then rotational blocking of the meniscus.

In order to reproduce the natural knee joint, the document WO 96/38103 has proposed a prosthesis in which the tibial plateau has two projecting studs, respectively anterior and posterior, which are intended to cooperate respectively with two indentations formed on the lower face of the intermediate component or insert.

The prosthesis proposed in this document, by virtue of the shape of the indentations, permits an at one and the same time lateromedial, anteroposterior and rotational movement of the insert on the tibial plateau. It nevertheless has a number of disadvantages to the extent that the rotation of the insert during flexion of the knee is effected on a vertical axis passing through the posterior stud of the tibial plateau. In other words, it is not possible here to reproduce the natural movement of the knee joint in flexion, according to which the rotation of the meniscus on the tibial plateau is effected on a substantially central axis.

Moreover, and as before, the arrangements provided in the area of the tibial plateau and of the insert do not permit rotational blocking of the insert during extension of the knee.

SUMMARY OF THE INVENTION

The invention therefore aims to provide a knee prosthesis with which it is possible to limit to a maximum the wear and tear on the insert subjected to the compressive and torsional forces, both from the femoral component and from the tibial component, while at the same time approximating the natural function of the knee joint.

To do this, the invention provides a prosthesis of the type comprising a tibial plateau which is anchored at the upper end of the tibia and on which there is attached an insert which is intended to cooperate with a femoral component anchored at the lower end of the femur.

This knee prosthesis is characterized in that the tibial plateau and the insert have complementary devices which are able to ensure:

in the position of extension, the rotational blocking of the insert on the tibial plateau;

and, during a flexion movement, firstly the translation of the insert in the anteroposterior direction and in the posteroanterior sense, and then the limited rotation of the insert on the tibial plateau.

In other words, the invention provides a knee prosthesis in which the tibial plateau and the insert are arranged in such a way as to permit the rotational blocking of the insert on the tibial plateau during extension of the knee, thereby limiting the wear and tear on the insert by blocking of its anteroposterior and rotational movement. Likewise, the arrangements ensure limited rotation of the insert on the tibial plateau starting from a certain degree of flexion of the tibia on the femur, and this with the dual purpose of limiting the wear and tear on the insert and of reproducing the natural function of the knee joint.

To stop the rotation in extension, while at the same time limiting the rotation in flexion, the complementary devices consist of:

on the one hand, a boss formed on the lower face of the insert in a substantially central position and intended to cooperate with an orifice formed on the upper face of the tibial plateau;

and, on the other hand, an indentation formed within the lower face of the insert, at its posterior edge, along an anteroposterior median axis in such a way as to cooperate with a projecting shoulder formed on the upper face of the tibial plateau.

To permit, during flexion of the tibia on the femur, firstly the translation in the posteroanterior sense, then the rotation of the insert on the tibial plateau, the boss is in the form of a cylinder portion and the orifice consists of a parallelepipedal posterior portion and a semi-cylindrical anterior portion having a diameter substantially equal to that of the boss.

This embodiment in fact permits a posteroanterior translational movement as well as a rotational movement, while at the same time prohibiting any lateral movement of the insert on the tibial plateau.

To make it possible to limit the rotation of the insert on the tibial plateau during flexion of the tibia on the femur, the projecting shoulder has the general shape of a U, of which the two branches widen out in the direction of the posterior edge of the tibial plateau, the shoulder being intended to cooperate with an indentation of the same general shape formed on the lower face of the insert, of which the thickness and size along the anteroposterior median axis are substantially equal to those of the shoulder, but with a greater spacing of the branches.

According to a first embodiment of the invention intended for the use of knee prostheses with posterior stabilization, the projecting shoulder and the complementary indentation are without any opening.

By contrast, according to another embodiment of the invention more particularly intended for the use of knee prostheses with retention of the posterior cruciate ligament, the projecting shoulder and the indentation are partially openworked.

Moreover, according to another characteristic of the invention, the spacing of the branches of the indentation is determined in such a way as to make it possible, during flexion of the tibia on the femur by at least 30°, to limit the rotation of the insert on the tibial plateau to more or less 15° in relation to the neutral position of the insert on the tibial plateau.

BRIEF DESCRIPTION OF THE DRAWINGS

The manner of realizing the invention, its function, and the advantages which derive from the invention, will become clearer from the following illustrative embodiments, with reference to the attached figures.

DETAILED DESCRIPTION OF THE INVENTION

Figure 1:
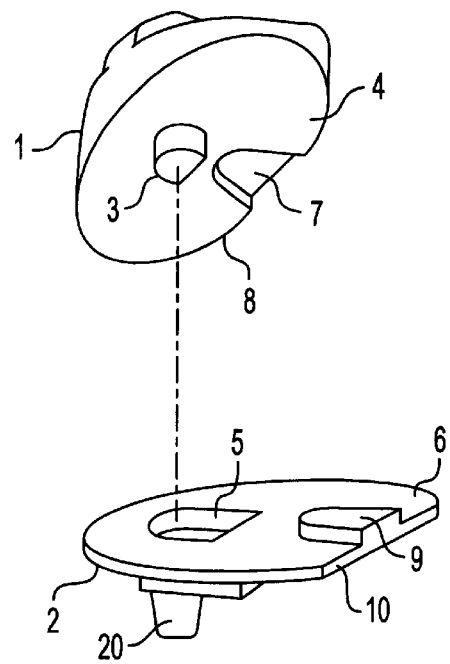
FIG. 1 is a diagrammatic perspective representation of the insert and of the tibial plateau according to a first embodiment of the invention, that is to say more particularly intended for fitting a knee prosthesis with posterior stabilization.

FIG. 1 shows an insert designated by the general reference 1 intended to be attached to a tibial plateau 2, the tibial plateau being implanted at the upper end of the tibia, and this within the more general context of implantation of a knee prosthesis with posterior stabilization.

Figure 11:
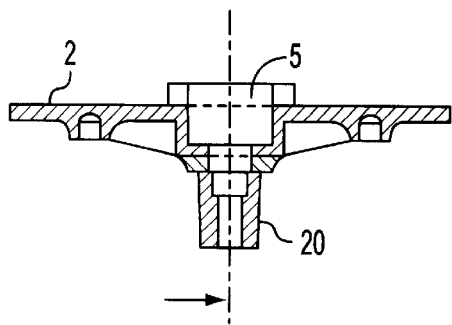
FIGS. 11 and 12 are diagrammatic cross-sections, respectively transverse and longitudinal, of the tibial plateau according to the invention.
Figure 12:
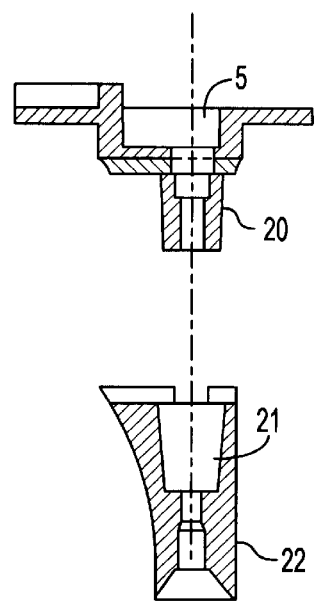

The insert and the tibial plateau have a general shape which is known to the skilled person and which is not the subject of the invention. However, as can be observed in FIGS. 11 and 12, the tibial plateau 2 has a central orifice 5 either blind or open, intended to receive the boss 3 of the insert, as is described hereinafter. Moreover, this orifice continues via a protrusion 20, in the shape of a Morse cone, intended to be received in an orifice of complementary shape 21 formed within the tibial stud 22, itself inserted in the medullary cavity of the tibia.

As has already been stated, the insert 1 is equipped with a boss 3 formed on its lower face 4 in a central position and intended to cooperate with the orifice 5 formed on the upper face 6 of the tibial plateau 2.

The insert 1 additionally has an indentation 7 formed within the lower face 4 in the area of the posterior edge 8 along an anteroposterior median axis, the indentation 7 being intended to cooperate with a shoulder 9 formed on the upper face of the tibial component 2 at the posterior edge 10.

according to the first embodiment represented in FIGS. 1 to 5, the boss 3 formed on the central part of the lower face of the insert is in the form of a cylinder portion.

This cylinder portion 3 is intended to cooperate with the orifice 5 which has a parallelepipedal posterior portion 11 and a semi-cylindrical anterior portion 12 having a diameter substantially equal to that of the cylinder portion 3.

Figure 4:
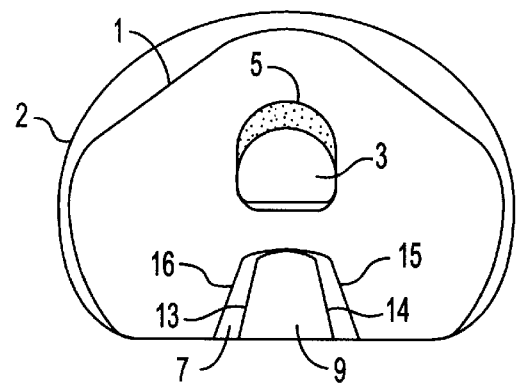
FIG. 4 is a plan view of the tibial plateau/insert assembly in the position of extension of the knee according to FIG. 1.

In the position of extension of the knee, as is shown in FIG. 4, the boss 3 is held locked in the anterior extreme part of the orifice 5, thereby prohibiting any rotational movement of the insert on the tibial plateau.

Figure 5A:
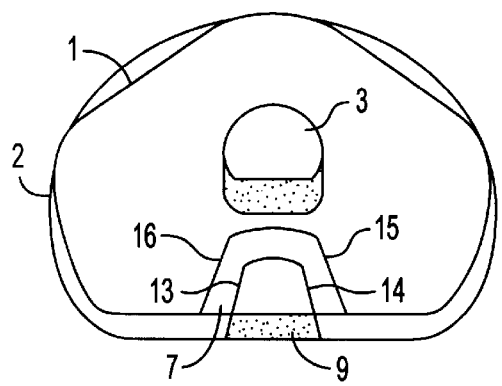
FIG. 5a is a plan view of the tibial plateau/insert assembly in the position of flexion before rotation of the tibia on the femur according to FIG. 2.
Figure 5B:
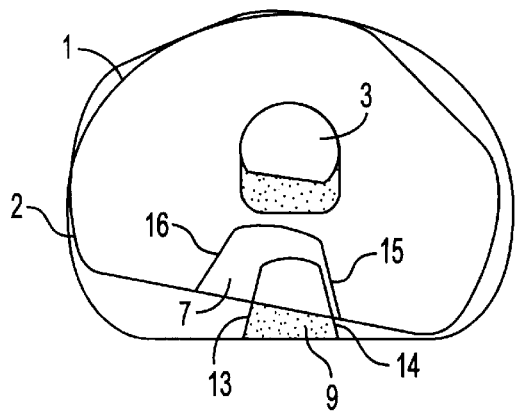
FIG. 5b is a plan view of the tibial plateau/insert assembly in the position of flexion after rotation of the insert on the tibial plateau.
Figure 6:
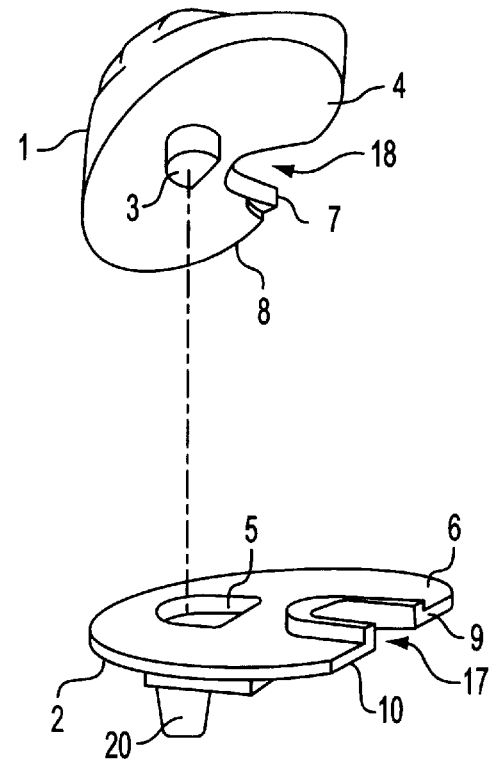
FIG. 6 is a diagrammatic perspective representation of another embodiment of the invention, using a knee prosthesis with retention of the posterior cruciate ligament of the knee.
Figures 7, 8:
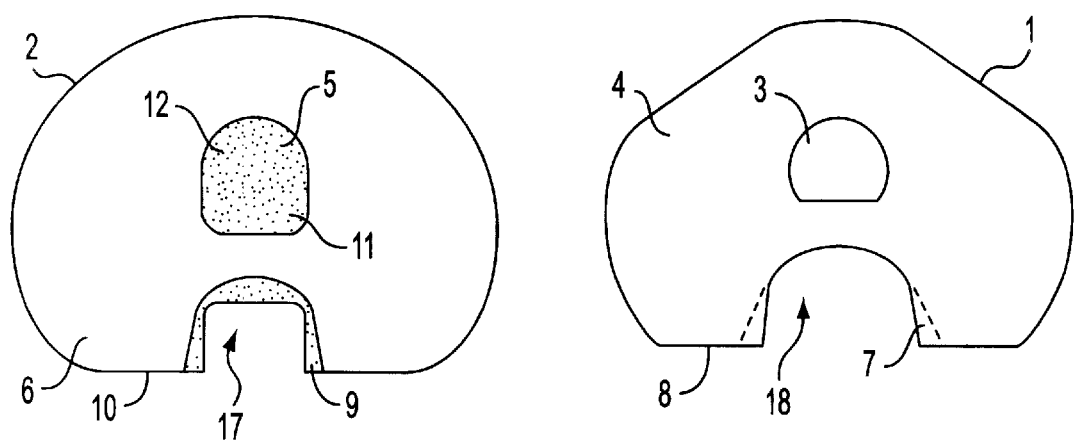
FIGS. 7 to 10 are views identical to FIGS. 2 to 5 according to the embodiment in FIG. 6.
Figure 9:
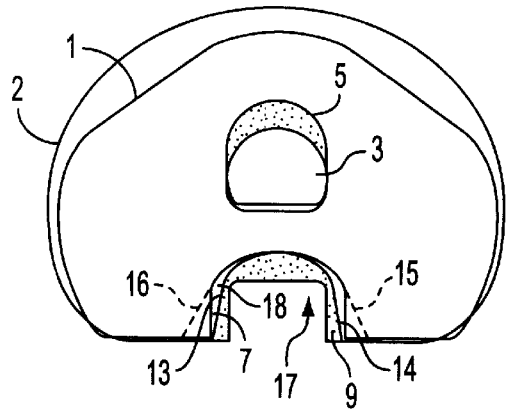
Figure 10A:
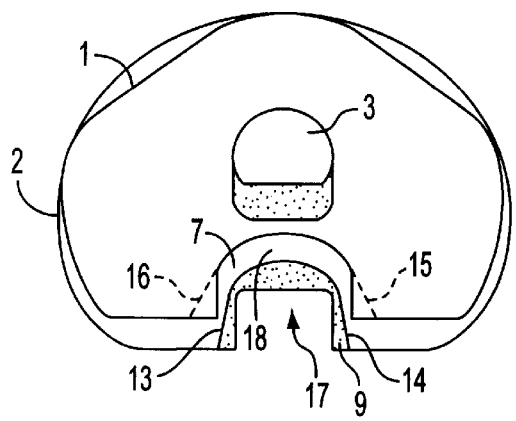
Figure 10B:
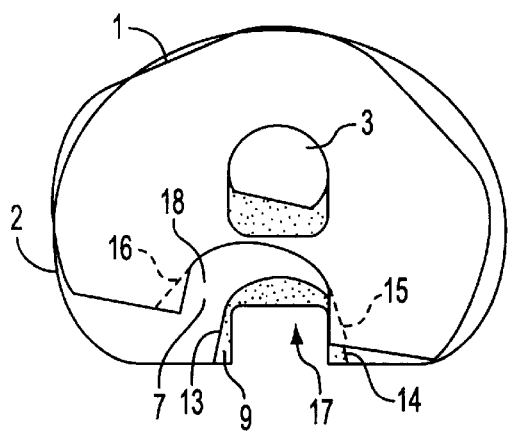

By contrast, in the position of flexion, the boss 3 is subjected to a translational movement in the posteroanterior sense to abut against the extreme posterior face of the opening 5, as is shown in FIG. 5a.

Moreover, according to another characteristic of the invention, the tibial plateau 2 has, in the area of its posterior edge 10, along the anteroposterior median axis, a projecting shoulder 9 having the general shape of a U, the two branches 13, 14 of which widen out from one another towards the edge 10.

As has already been stated, this projecting shoulder 9 is intended to cooperate with an indentation 7 formed on the lower face of the insert in the area of its posterior edge.

Figure 2:
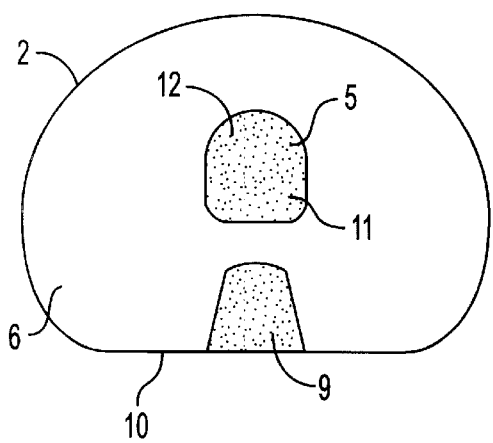
FIG. 2 is a diagrammatic plan view of the tibial plateau according to FIG. 1.
Figure 3:
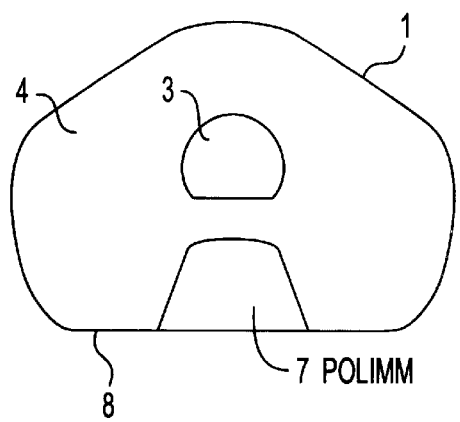
FIG. 3 is a bottom view of the insert according to FIG. 1.

As FIGS. 2 and 3 show, the projecting shoulder 9 and the indentation 7 have the same general U shape, the thickness and size along the anteroposterior median axis of the indentation being substantially equal to those of the shoulder, but the spacing of the branches 15, 16 being greater in relation to the branches 13, 14.

In practice, the spacing of the branches is determined so as to make it possible to limit the rotation of the insert on the tibial plateau to more or less 15° in relation to a neutral position of the insert on the tibial plateau, that is to say in relation to an anteroposterior median axis after flexion of the tibia on the femur by at least 30°.

When the knee is in the position of extension, the indentation 7 is positioned abutting against the projecting shoulder FIG. 4. By contrast, during a movement of flexion, the indentation 7 is subjected to a movement of posteroanterior translation, of which the displacement is equal to that of the boss 3 in the orifice 5.

When the boss is in abutment against the anterior end of the orifice, corresponding to a flexion substantially of the order of 30°, the insert can undergo rotation in relation to the tibial plateau, this rotation being limited approximately to more or less 15° in relation to the anteroposterior median axis by of the arms of the U of the indentation coming into contact with the arms of the corresponding U of the projecting shoulder.

Thus, a movement of flexion of the femur on the tibia is obtained during which the insert first undergoes a movement of posteroanterior translation, then a rotation of more or less 15° in relation to the tibial plateau, thereby making it possible not only to reproduce the natural knee joint, but also to limit the wear and tear on the insert.

FIGS. 6 to 10 show another embodiment of the invention, more particularly intended for knee prostheses in which the posterior cruciate ligament of the knee is retained. According to this embodiment, the shoulder 9 and the indentation 7 are both partially openworked 17, 18 in order to permit the passage of the ligament.

As the figures show, the same results are achieved during a movement of flexion or extension.

The advantages will be clear from the description.

Thus, the reproduction of the natural movement of the knee joint is emphasized, according to which, in the position of extension, the insert is maintained fixed in relation to the tibial plateau, and, in the position of flexion, the insert undergoes a movement of anteroposterior translation and then rotation.

Figure 13:
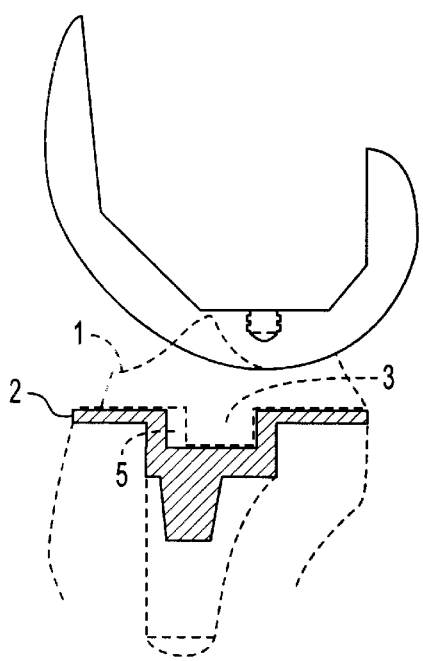
FIGS. 13 and 14 are diagrammatic cross-sections of the tibial plateau equipped with the insert according to the invention, respectively in extension and in flexion.
Figure 14:
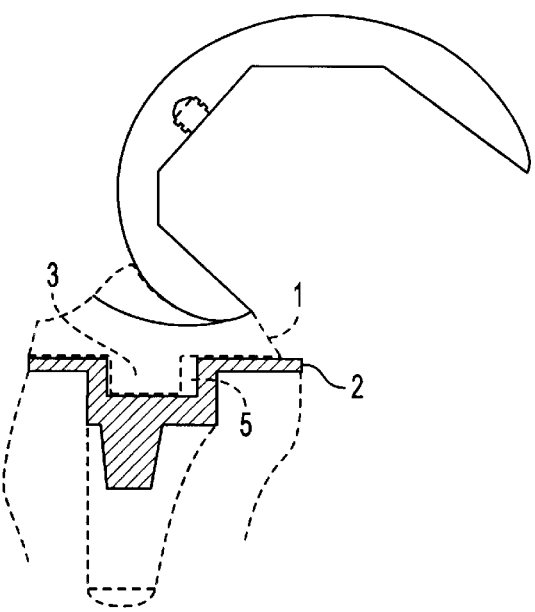

This translational movement from rear to front has been shown in FIGS. 13 and 14.

In addition, the arrangements provided on the insert and on the tibial plateau make it possible to greatly limit the wear and tear on the insert.

What is claimed is:

1. A once prosthesis comprising:
   a tibial plateau for anchoring to an upper end of a tibia, the tibial plateau comprising an orifice and a projection;
   an insert moveably disposed on the tibial plateau adapted to cooperate with a femoral component anchored to a lower end of a femur, the insert comprising a boss and an indentation;
   wherein the insert moveably engages the tibial plateau such that the boss extends at last partially into the orifice and the projection extends at least partially into the indentation.

2. The knee prosthesis of claim 1, wherein the boss of the insert comprises a semi-cylindrical anterior portion and a flat posterior portion, protrudes from a tibial plateau engaging surface, and is approximately centrally disposed on the tibial plateau engaging surface of the insert.

3. The knee prosthesis of claim 2, wherein the indentation of the insert extends into the tibial plateau engaging surface and is disposed on an anteroposterior medial axis.

4. The knee prosthesis of claim 2, wherein the insert is rotatable about the boss with respect to the tibial plateau in at least a first direction and at least a second direction.

5. The knee prosthesis of claim 3, wherein the insert is prevented from further rotating in the first direction when a shoulder of the projection of the tibial plateau engages a shoulder of the indentation of the insert and wherein the insert is prevented from further rotating in the second direction when a shoulder of the projection of the tibial plateau engages a shoulder of the indentation of the insert.

6. The knee prosthesis of claim 1, wherein the boss of the insert comprises a semi-cylindrical anterior portion and flat posterior portion and wherein the orifice of the tibial plateau comprises a parallelepipedal posterior portion and a semi-cylindrical anterior portion.

7. The knee prosthesis of claim 6, wherein the semi-cylindrical anterior portion of the orifice comprises a diameter which is substantially equal to a diameter of the semi-cylindrical anterior portion of the boss.

8. The knee prosthesis of claim 1, wherein the boss of the insert is in the form of a partially cylindrical portion having a flat surface and wherein the indentation generally comprises a U-shape.

9. The knee prosthesis of claim 8, wherein the orifice of the tibial plateau is in the form of a semi-cylindrical portion having a flat surface and wherein the projection generally comprises a U-shape.

10. The knee prosthesis of claim 1, wherein the orifice of the tibial plateau is in the form of a semi-cylindrical portion having a flat posterior surface and wherein the projection generally comprises a U-shape.

11. The knee prosthesis of claim 1, wherein the projection of the tibial plateau generally comprises a U-shape and comprises an opening which allows the passage of a posterior cruciate ligament, and wherein the indentation extends into the insert a distance which is approximately equal to a length of the projection.

12. The knee prosthesis of claim 11, wherein the indentation of the insert generally comprises a U-shape and comprises an opening which allows the passage of a posterior cruciate ligament.

13. A knee prosthesis comprising:
    a tibial plateau for anchoring to an upper end of a tibia, the tibial plateau comprising a projection and an approximately centrally disposed orifice having a semi-cylindrical anterior portion and a parallelepipedal posterior portion;
    an insert moveably disposed on the tibial plateau and adapted to cooperate with a femoral component anchored to a lower end of a femur, the insert comprising a boss having an indentation and a semi-cylindrical anterior portion;
    wherein the insert moveably engages the tibial plateau such that the boss extends at least partially into the orifice.

14. The knee prosthesis of claim 13, wherein the boss of the insert protrudes beyond a tibial plateau engaging surface of the insert and is approximately centrally disposed on the tibial plateau engaging surface.

15. The knee prosthesis of claim 14, wherein the insert further comprises an indentation which extends into a tibial plateau engaging surface of the insert and is disposed on an anteroposterior medial axis.

16. The knee prosthesis of claim 13, wherein the insert is rotatable about the boss with respect to the tibial plateau in at least a first direction and at least a second direction.

17. The knee prosthesis of claim 16, wherein the insert further comprises an indentation and wherein the tibial plateau further comprises a projection, such that the insert is prevented from further rotating in the first direction when a shoulder of the projection of the tibial plateau engages a shoulder of the indentation of the insert and wherein the insert is prevented from further rotating in the second direction when a shoulder of the projection of the tibial plateau engages a shoulder of the indentation of the insert.

18. The knee prosthesis of claim 17, wherein the indentation of the insert generally comprises a U-shape.

19. The knee prosthesis of claim 18, wherein the projection of the tibial plateau generally comprises a U-shape.

20. The knee prosthesis of claim 17, wherein the projection of the tibial plateau generally comprises a U-shape and comprises an opening which allows the passage of a posterior cruciate ligament.

21. The knee prosthesis of claim 17, wherein the indentation of the insert generally comprises a U-shape and comprises an opening which allows the passage of a posterior cruciate ligament.

22. The knee prosthesis of claim 13, wherein the semi-cylindrical anterior portion of the orifice comprises a diameter which is substantially equal to a diameter of the semi-cylindrical portion of the boss.

23. A knee prosthesis comprising:
    a tibial plateau for anchoring to an upper end of a tibia, the tibial plateau comprising an approximately centrally disposed orifice and a projection;
    an insert moveably disposed on the tibial plateau adapted to cooperate with a femoral component anchored to a lower end of a femur, the insert comprising an approximately centrally disposed boss for engaging the orifice and an indentation;

wherein the insert moveably engages the tibial plateau such that the boss extends at least partially into the orifice and wherein the insert is rotatable about an axis.

24. A knee prosthesis comprising:

a tibial plateau for anchoring to an upper end of a tibia, the tibial plateau comprising an orifice and a projection, the projection comprising a U-shape having branches which widen out in a direction of a posterior edge;

an insert moveably disposed on the tibial plateau adapted to cooperate with a femoral component anchored to a lower end of a femur, the insert comprising an approximately centrally disposed boss and an indentation, the indentation comprising a U-shape having branches which widen out in a direction of a posterior edge and being disposed on a posterior edge of the insert along an anteroposterior median axis;

wherein the insert moveably engages the tibial plateau such that the boss extends at least partially into the orifice and the projection extends at least partially into the indentation.

25. The knee prosthesis of claim 24, wherein the insert is rotatable about the boss with respect to the tibial plateau in at least a first direction and at least a second direction.

26. The knee prosthesis of claim 25, wherein the insert is prevented from further rotating in the first direction when a shoulder of the projection of the tibial plateau engages a shoulder of the indentation of the insert and wherein the insert is prevented from further rotating in the second direction when a shoulder of the projection of the tibial plateau engages a shoulder of the indentation of the insert.

27. The knee prosthesis of claim 26, wherein the insert is rotatable approximately 15° in the first direction and approximately 15° in the second direction.

28. A knee prosthesis comprising:

a tibial plateau for anchoring to an upper end of a tibia, the tibial plateau comprising an orifice and a projection, the projection being partially openworked;

an insert moveably disposed on the tibial plateau adapted to cooperate with a femoral component anchored to a lower end of a femur, the insert comprising an approximately centrally disposed boss and an indentation, the indentation being partially openworked and disposed on a posterior edge of the insert along an anteroposterior median axis;

wherein the insert moveably engages the tibial plateau such that the boss extends at least partially into the orifice and the projection extends at least partially into the indentation.

* * * * *